United States Patent [19]
Anderson et al.

[11] Patent Number: 6,030,782
[45] Date of Patent: *Feb. 29, 2000

[54] COVALENT ATTACHMENT OF NUCLEIC ACID MOLECULES ONTO SOLID-PHASES VIA DISULFIDE BONDS

[75] Inventors: Steve Anderson, Princeton, N.J.; Yu-Hui Rogers, Damascus, Md.

[73] Assignee: Orchid Biocomputer, Inc., Princeton, N.J.

[ * ] Notice: This patent is subject to a terminal disclaimer.

[21] Appl. No.: 08/975,862

[22] Filed: Nov. 21, 1997

Related U.S. Application Data

[63] Continuation-in-part of application No. 08/812,010, Mar. 5, 1997, Pat. No. 5,837,860.

[51] Int. Cl.⁷ ........................................................ C12Q 1/68
[52] U.S. Cl. ............................................. 435/6; 536/24.3
[58] Field of Search ................................ 435/6; 536/24.3

[56] References Cited

U.S. PATENT DOCUMENTS

| | | |
|---|---|---|
| 5,302,509 | 4/1994 | Cheesman . |
| 5,897,955 | 4/1999 | Drumheller .............................. 428/422 |

FOREIGN PATENT DOCUMENTS

| | | |
|---|---|---|
| 2650840 | 2/1991 | France . |
| 92/15712 | 9/1992 | WIPO . |
| 95/17676 | 6/1995 | WIPO . |

OTHER PUBLICATIONS

Carlsson, J. et al., "Solid Phase Disulfide Oxides: A New Approach to Reversible Immobilization and Covalent Chromatography of Thiol Compounds," *Biotech. Applied Biochem.* 14:114–120 (1991).

Chu, B.C.F. et al., "Ligation of Oligonucleotides to Nucleic Acids or Proteins via Disulfide Bonds," *Nucleic Acids Res.* 16: 3671–3691 (1988).

Fahy, E. et al., "Design and Synthesis of Polyacrylamide–based Oligonucleotide Supports for Use in Nucleic Acid Diagnosis" *Nucleic Acids Res.* 21: 1819–1826 (1993).

Holmstrom, K. et al., "A Highly Sensitive and Fast Nonradioactive Method for Detection of Polymerase Chain Reaction Products," *Anal Biochem.* 209:278–283 (1993).

Maskos, U. et al., "Oligonucleotide Hybridisations on Glass Supports: A Novel Linker for Oligoncleotide Synthesis and Hubridisation Properties of Oligonucleotides Synthesised in situ," *Nucl. Acids Res.* 20:1679–1684 (1992).

Newton, C.R. et al., "The Production of PCR Products with 5' Single–Stranded Tails using Primers that Incorporated Novel Phosphoramidite Intermediates," *Nucl. Acids Res.* 21:1155–1162 (1993).

Rasmussen, S.R. et al., "Covalent Attachment of DNA onto Polystyrene Microwells: The Molecules are only Bound at the 5' End," *Anal. Biochem.* 198:138–142 (1991).

Running, J.A. et al., "A Procedure for Productive Coupling of Synthetic Oligonucleotides to Polystyrene Microtiter Wells for Hybridization Capture," *BioTechniques* 8:276–277 (1990).

Sliwkowski, M.X. et al., "Resolution of Sulphydryl Oxidase from gama–Glutamyltrransferase in Bovine Milk by Covalent Chromatography on Cysteinylsuccinamidopropyl–Glass," *Biochem. J.* 209:731–739 (1983).

*Primary Examiner*—Scott W. Houtteman
*Attorney, Agent, or Firm*—Karlow Springut & Bressler

[57] ABSTRACT

Methods for the covalent, specific and reversible immobilization of nucleic acid molecules onto solid-phases by means of a reversible disulfide bond for nucleic acid molecule array preparation are described. These methods can be used to prepare reusable nucleic acid molecule arrays with hilgh specificity and high efficiency.

31 Claims, 2 Drawing Sheets

| ROW # | | | ROW # | | | ROW # | | | ROW # | |
|---|---|---|---|---|---|---|---|---|---|---|
| 1 | 2 | 3 | 1 | 2 | 3 | 1 | 2 | 3 | 1 | 2 |

SLIDE 1　　　SLIDE 2　　　SLIDE 3　　　SLIDE 4

FIG.2

COVALENT ATTACHMENT OF NUCLEIC ACID MOLECULES ONTO SOLID-PHASES VIA DISULFIDE BONDS

CROSS REFERENCE TO RELATED APPLICATION

This application is a continuation-in-part of U.S. patent application Ser. No. 08/812,010, filed on Mar. 5, 1997, now U.S. Pat. No. 5,837,860.

FIELD OF THE INVENTION

The present invention relates to a method for immobilizing nucleic acid molecules to solid-phases. More specifically, the present invention describes a method to covalently immobilize 5'-sulfhydryl or 5'-disulfide modified nucleic acid molecules to a solid phase by means of a reversible disulfide bond. The present invention also describes a method to covalently immobilize 3'-sulfhydryl or 3'-disulfide modified nucleic acid molecules to a solid phase by means of a reversible disulfide bond.

BACKGROUND OF THE INVENTION

The analysis of the structure, organization and sequence of nucleic acid molecules is of profound importance in the prediction, diagnosis and treatment of human and animal disease, in forensics, in epidemiology and public health, and in the elucidation of the factors that control gene expression and development. Methods for immobilizing nucleic acids are often important in these types of analyses. Three areas of particular importance involve hybridization assays, nucleic acid sequencing, and the analysis of genomic polymorphisms.

I. Nucleic Acid Hybridization

The capacity of a nucleic acid "probe" molecule to hybridize (i.e. base pair) to a complementary nucleic acid "target" molecule forms the cornerstone for a wide array of diagnostic and therapeutic procedures.

Hybridization assays are extensively used in molecular biology and medicine. Methods of performing such hybridization reactions are disclosed by, for example, Sambrook, J. et al. (In: *Molecular Cloning: A Laboratory Manual*, Cold Spring Harbor laboratory Press, Cold Spring Harbor, N.Y. (1989)), Haymes, B. D., et al. (In: *Nucleic Acid Hybridization, A Practical Approach*, IRL Press, Washington, D.C. (1985)) and Keller, G. H. and Manak, M. M. (In: *DNA Probes, Second Edition*, Stockton Press, New York, N.Y. (1993)) which references are incorporated herein by reference.

Many hybridization assays require the immobilization of one component to a solid support. Nagata et al. described a method for quantifying DNA which involved binding unknown amounts of cloned DNA to microtiter wells in the presence of 0.1 M $MgCl_2$ (Nagata et al., *FEBS Letters* 183: 379–382 (1985). A complementary biotinylated probe was then hybridized to the DNA in each well and the bound probe measured colorimetrically. Dahlen, P. et al. have discussed sandwich hybridization in microtiter wells usling, cloned capture DNA adsorbed to the wells (Dahlen, P. et al., *Mol. Cell. Probes* 1: 159–168 (1987). An assay for the detection of HIV-1 DNA using PCR amplification and capture hybridization in microtiter wells has also been discussed (Keller, G. H. et al., *J. Clin. Microbiol.* 29: 638–641 (1991). The NaCl-mediated binding of oligomers to polystyrene wells has been discussed by Cros et al. (French Patent No. 2,663,040) and by Nikiforov et al. (*PCR Methods Applic.* 3: 285–291 (1994). The cationic detergent-mediated binding of oligomers to polystyrene wells has been described by Nikiforov et al., *Nucleic Acids Res.* 22: 4167–4175 (1994).

II. Analysis of Single Nucleotide DNA Polymorphisms

Many genetic diseases and traits (i.e. hemophilia, sickle-cell anemia, cystic fibrosis, etc.) reflect the consequences of mutations that have arisen in the genomes of some members of a species through mutation or evolution (Gusella, J. F., *Ann. Rev. Biochem.* 55:831–854 (1986)). In some cases, such polymorphisms are linked to a genetic locus responsible for the disease or trait; in other cases, the polymorphisms are the determinative characteristic of the condition.

Single nucleotide polymorphisms differ significantly from the variable nucleotide type polymorphisms ("VNTRs"), that arise from spontaneous tandem duplications of di- or tri-nucleotide repeated motifs of nucleotides (Weber, J. L., U.S. Pat. No. 5,075,217; Armour, J. A. L. et al., *FEBS Lett.* 307:113–115 (1992); Jones, L. et al., *Eur. J. Haematol.* 39:144–147 (1987); Horn, G. T. et al., PCT Application No. WO91/14003; Jeffreys, A. J., U.S. Pat. No. 5,175,082); Jeffres. A. J. et al., *Amer. J. Hum. Genet.* 39:11–24 (1986); Jeffreys, A. J. et al., *Nature* 316:76–79 (1985); Gray, I. C. et al., *Proc. R. Acad. Soc. Lond.* 243:241–253 (1991); Moore, S. S. et al., *Genomics* 10:654–660 (1991); Jeffreys, A. J. et al., *Anim. Genet.* 18:1–15 (1987); Hillel, J. et al., *Anim. Genet.* 20:145–155 (1989); Hillel, J. et al., *Genet.* 124:783–789 (1990)), and from the restriction fragment length polymorphisms ("RFLPs") that comprise variations which alter the lengths of the fragments that are generated by restriction endonuclease cleavage (Glassberg, J., UK Patent Application No. 2135774; Skolnick, M. H. et al., *Cytogen. Cell Genet.* 32:58–67 (1982); Botsten, D. et al., *Ann. J. Hum. Genet.* 32:314–331 (1980); Fischer, S. G. et al. (PCT Application No. WO90/13668); Uhlen, M., (PCT Application No. WO90/11369)).

Because single nucleotide polymorphisms constitute sites of variation flanked by regions of invariant sequence, their analysis requires no more than the determination of the identity of the single nucleotide present at the site of variation; it is unnecessary to determine a complete gene sequence for each patient. Several methods have been developed to facilitate the analysis of such single nuicleotide polymorphisms.

Mundy, C. R. (U.S. Pat. No. 4,656,127), for example, discusses a method for determining the identity of the nucleotide present at a particular polvymorphic site that employs a specialized exonuclease-resistant nucleotide derivative. A primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. The Mundy method has the advantage that it does not require the determination of large amounts of extraneous sequence data. It has the disadvantages of destroying the amplified target sequences, and unmodified primer and of being extremely sensitive to the rate of polymerase incorporation of the specific exonuclease-resistant nucleotide being used.

Cohen, D. et al., (French Patent 2,650,840; PCT Application No. WO91/02087) discuss a solution-based method for determining the identity of the nucleotide of a polymorphic site. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

The Genetic Bit Analysis method or GBA™ method is described by Goelet, P. et al. (PCT Application No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent No. 2,650,840; PCT Application No. WO91/02087) the method of Goelet, P. et al. is preferably a heterogeneous phase assay, in which the primer or the target molecule is immobilized to a solid phase. It is thus easier to perform, and more accurate than the method discussed by Cohen.

Cheesman, P. (U.S. Pat. No. 5,302,509) describes a method for sequencing a single stranded DNA molecule using fluorescently labeled 3'-blocked nucleotide triphosphates. An apparatus for the separation, concentration and detection of a DNA molecule in a liquid sample has been recently described by Ritterband, et al. (PCT Patent Application No. WO95/17676).

An alternative approach, the "Oligonucleotide Ligation Assay" ("OLA") (Landegren, U. et al., *Science* 241:1077–1080 (1988)) has also been described as capable of detecting single nucleotide polymorphisms. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered usilng avidin, or another biotin ligand. Nickerson, D. A. et al. have described a nucleic acid detection assay that combines attributes of PCR and OLA (Nickerson, D. A. et al., *Proc. Natl. Acad. Sci. (U.S.A.)* 87:8923–8927 (1990)). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Several primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvänen, A. -C., et al., *Genomics* 8:684–692 (1990); Kuppuswamy, M. N. et al., *Proc. Natl. Acad. Sci. (U.S.A.)* 88:1143–1147 (1991); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvänen, A. -C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA™ method. In addition, for some loci, incorporation of an incorrect deoxynucleotide can occur even in the presence of the correct dideoxyntucleotide (Komher, J. S. et al., *Nucl. Acids. Res.* 17:7779–7784 (1989)). Such deoxynucleotide misincorporation events may be due to the Km of the DNA polymerase for the mispaired deoxy-substrate being comparable, in some sequence contexts, to the relatively poor Km of even a correctly base paired dideoxy-substrate (Kornberg, A., et al., In: *DNA Replication*, Second Edition (1992), W. H. Freeman and Company, New York; Tabor, S. et al., *Proc. Natl. Acad. Sci. (U.S.A.)* 86:4076–4080 (1989)). This effect would contribute to the background noise in the polymorphic site interrogation.

III. Methods of Immobilizing Nucleic Acids to a Solid-Phase

Several of the above-described methods involve procedures in which one or more of the nucleic acid reactants are immobilized to a solid support. Currently, 96-well polystyrene plates are widely used in solid-phase immunoassays, and several PCR product detection methods that use plates as a solid support have been described. The most specific of these methods require the immobilization of a suitable olionucleotide probe into the microtiter wells followed by the capture of the PCR product by hybridization and colorimetric detection of a suitable hapten. It would be desirable to have an improved immobilization method that could be used to bind nucleic acid molecules to polystyrene or glass such that their capacity to be used for hybridization, sequencing, or polymorphic analysis would be retained, and which would be rapid, convenient to use, inexpensive, reversible and reusable. The present invention provides such an improved method.

Covalent disulfide bonds have been previously used to immobilize both proteins and oligonucleotides. Carlsson, J. et al., (*Biotech. Applied Biochem.* 14:114–120 (1991)) discloses a method for the reversible immobilization of thiolated proteins and peptides to an agarose bead by means of a disulfide bond. In that method, the disulfide bond is formed between a thiol containing protein and a thiol-derivatized agarose bead. The reference also discloses that the disulfide bond is reversible in the presence of an excess of dithiothreitol. Chu, B. C. F. et al., (*Nucleic Acids Res.* 16: 3671–3691 (1988)) discloses a method for coupling oligonucleotides to nucleic acids or proteins via cleavable disulfide bonds. Prior to the coupling reaction, the oligonucleotides are modified by adding a cystamine group to the 5' phosphate by means of a phosphoramadite bond. Sliwkowski, M. X. et al., (*Biochem. J.* 209: 731–739 (1983)) discloses a metlhod of covalent chromatography wherein proteins are immobilized to cysteinylsuccinimidoproyl glass beads through reversible disulfide bond interaction.

Fahy, E. et al., (*Nucleic Acids Res.* 21: 1819–1826 (1993)) describes the synthesis of 5'-bromacetyl and 5'-thiol oligonculeotide derivatives and the covalent immobilization of these oligoinucleotide derivatives via thioester bonds to sultlbydryl- and bromacetyl-modified polyacrylamide supports. The disadvantage of this method is that the covalent bond is not reversible.

The present invention describes a novel method for immobilizing nucleic acid molecules to a solid-phase by means of a reversible, covalent dissulfide bond. This simple, two-step method has the specificity and efficiency needed to prepare DNA arrays.

SUMMARY OF THE INVENTION

The present invention provides a method to covalently couple nucleic acid molecules to a solid-phase by means of reversible disulfide bond interactions. The immobilized molecules can be used for hybridization, seqcuencing, or polymorphic analysis.

In detail, the invention provides a method for coupling a nucleic acid molecule to a solid phase which comprises coupling a sulfhydryl or disulfide modified nucleic acid molecule to a mercaptosilane or disulfidesilane coated solid-phase. The sulfhydryl or disulfide modification of the nucleic acid molecule may be at either (or both) the 5' or 3' terminus of the molecule.

The invention particularly pertains to the embodiments wherein the attachment is by means of a disulfide exchange reaction between the mercaptosilane coated solid-phase and the 5' and/or 3' disulfide modified nucleic acid molecule.

The invention additionally pertains to the embodiments wherein the attachment is by means of a disulfide formation reaction between the disulfidesilane coated solid-phase and a 5' and/or 3' sulfhydryl modified nucleic acid molecule.

The invention further pertains to the embodiment wherein the coupled nucleic acid molecules are arranged in a reusable nucleic acid molecule array.

BRIEF DESCRIPTION OF THE FIGURES

FIG. 2 illustrates the suitability of ink-jet printing for preparing an oligonucleotide array using the present method.

DETAILED DESCRIPTION OF THE INVENTION

Figure 1:
FIG. 1 depicts the direct detection of a GBA signal using the disulfide attachment method.

I. The Immobilization of Nucleic Acid Molecules

The present invention concerns a method for immobilizing nucleic acid molecules onto a solid-phase. Recently, several methods have been proposed as suitable for immobilizing an oligonucleotide to a solid support. Holmstrom, K. et al., for example, exploit the affinity of biotin for avidin and streptavidin, and immobilize biotinylated nucleic acid molecules to avidin/streptavidin coated supports Holmstrom, K. et al., *Anal. Biochem.* 209:278–283 (1993)). Another method requires the precoating of the polystyrene or glass solid phases with poly-L-Lys or poly-L-Lys, Phe, followed by the covalent attachment of either amino- or sulfhydryl-modified oligonucleotides using bi-functional crosslinking reagents. Like the present invention, both methods require the use of modified oliconucleotides as well as a pretreatment of the solid phase; however, the current invention has the added advantage in that the attachment is by means of a reversible, covalent disulfide bond (Running, J. A. et al., *BioTechniques* 8:276–277 (1990); Newton, C. R. et al. *Nucl. Acids Res.* 21:1155–1162 (1993)).

Kawai, S. et al. describes an alternative method in which short oligoyonucleotide probes were ligated together to form multimers and these were ligated into a phagemid vector (Kawai, S. at al., *Anal. Biochem.* 209:63–69 (1993)). The oligonucleotides were immobilized onto polystyrene plates and fixed by UV irradiation at 254 nm. A method for the direct covalent attachment of short, 5'-phosphorylated primers to chemically modified polvstyrene plates ("Covalink" plates, Nunc) has also been proposed by Rasmussen, S. R. et al., (*Anal. Biochem.* 198:138–142 (1991)). The covalent bond between the modified oligonucleotide and the solid phase surface is created by a condensation reaction with a water-soluble carbodiimide. The Rasmussen method claims a predominantly 5'-attachment of the oligonucleotides via their 5-phosphates; however, it requires the use of specially prepared, expensive plates. The method of the present invention departs from such methods, in not requiring unstable and difficult to manipulate crosslinking reagents.

Maskos, U. et al. describes a method to synthesize oligonucleotides directly onto a glass support (Maskos, U. et al., *Nucl. Acids Res.* 20:1679–1684 (1992)). According to this method, a flexible linker with a primary hydroxyl group is bound to the solid support via a glycidoxypropyl silane, wherein the primary hydroxyl group serves as the starting point for the oligonucleotide synthesis. The disadvantages of this method are that the reaction is not reversible and the oligonucleotides leak from the solid surface during manipulation.

The present invention provides a method for covalently attaching a modified nucleic acid molecule to a solid support. In a preferred embodiment, the nucleic acid molecule will be modified such that it contains one or more suliflydryl or disulfide groups. Such modification will preferably be at a 3' or 5' carbon of a sugar moiety of the nucleic acid molecule. Thus, in such preferred embodiment, the modification may be one or more 3' sulfhydryl group(s), 3' disulfide group(s), 5' sulflhydryl g,roup(s), or 5' disulfide group(s). Most preferably, suich modification iwill be at a modification of the sugar mioiety of a terminal nucleotide residue.

The present method provides two distinct advantages over other covalent attachment chemistries for oligo array preparation. First, the mercaptosilanized surface of the present method provides a very hydrophobic surface which allows oligonucleotide probe droplets to form at specific and localized positions on the solid surface. Thus, for example, multiple probes can be patterned simultaneously on the surface using a robotic liquid delivery system or ink-jet printing technique with no cross contamination between probes, even at a high probe density (10,000 probes/cm$^2$). Accordingly, the process can be easily automated and scaled-up using an off-the-shelf robot or ink-jet printing instrument.

Standard covalent attachment chemistries require the use of photolithographic and laser patterning techniques which require multiple masking and lifting steps for high density DNA array preparation. Unlike traditional techniques, the present method does not require the use of expensive crosslinking agents. These crosslinking agents are difficult to use because of their sensitivity to air and humidity. Therefore, the present method provides a new, efficient and inexpensive method for DNA array preparation, and particularly for large scale DNA array preparation.

The present invention describes a specific, highly efficient and reversible method to covalently attach nucleic acid molecules in an end specific manner to a solid-phase. The covalent bond described in the present invention is a reversible disulfide bond; however, other reversible covalent bonds may be used. End specific attachment ensures that the full sequence of the immobilized oligonucleotide is accessible for a desired biochemical reaction.

The covalent attachment of the present invention can be distinguished from other means of attachment, such as van der Waals interaction and ion-ion interactions. A covalent disulfide bond is the preferred embodiment because the reaction chemistry is efficient, easy to manipulate, specific and stable. Thus, uinlike other attachment means, the covalently immobilized oligonucleotide will not be released from the solid-phase during subsequent wash steps. The covalent attachment generally provides more stable binding than noncovalent attachment under elevated temperatures and upon other chemical treatment; thus, giving more flexibility for use in biochemical processes. However, the covalently immobilized oligonucleotide can be released from the solid-phase, if needed, by washing with a solution containing a suitable reducing agent.

While an strong to mild reducing agent may be used to reverse the disulfide bond, the preferred reducing agents are dithiothreitol and mercaptoethanol. Dithiothreitol is an especially preferred reducing agent because it is capable of forming an internal disulfide bond in the form of a stable six-member ring, which drives the reaction towards completion.

The sulfhydryl and/or disulfide modified nucleic acid molecules, described in the present invention, may be either genomic DNA (i.e., DNA containing a non-translated region), cDNA (i.e., DNA lacking non-translated regions) or RNA; the nucleic acid molecule may also be either single or double stranded. While any sulfhydryl and/or disulfide modified nucleic acid molecule may be immobilized usinig the present invention, the preferred nucleic acid molecule of the present invention is a sullflhydryl and/or disulfide modified single-stranded synthetic oligonucleotide. The method for making a synthetic oligonucleotide has been previously described by Gait, M. J. (*Oligonucleotide Synthesis, A Practical Approach*, IRL Press Ltd., Oxford (1984)) and Sinha, N. D. et al. (*Nucl. Acids Res.* 12:4539–4557 (1984)) (both herein incorporated by reference).

Synthesis of 5'-sulfhydryl or 5'-disulfide modified oligonucleotides of about 10 to about 250 nucleotides in length may be performed on an ABI 392 DNA/RNA synthesizer according to phosphi-amidite chemistry. The disulfide linkage is added to the 5'-terminus of the oligonucleotide using 5' thiol-Modifiers, such as 1-O-dimethoxytrityl-hexyl-disulfide, 1'-[(2-cyano-ethyl)-(N,N-diisopropyl)]-phosphoramidite, etc. The sulfhydyl group can be generated by treating the disulfide modified oligonucleotide with a reducing agent such as dithiothreitol (DTT).

The synthesis of 3'-disulfide or 3'-sulfhydryl oligonucleotides may be performed on an ABI 392 DNA/RNA Synthesizer according to phosphoramidite chemistry. The distulfide linkage is added to the 3'-terminus of the oligonucleotide using 3' thiol-Modifiers or 3' thiol-Modifiers CPG, such as, 1-O-dimethoxytrityl-hexyl-disulfide, 1'-[(2-cyanoethyl)-(N,N-diisopropyl)]-phosplhoramidite, 1-O-dimethoxytriyl-propyl-disulfide, 1'-succinoyl-long chain alkylamino-CPG, etc. The sulfhydryl group can be generated by treating the disulfide modified oligonucleotide with a reducing agent such as dithiothreitol (DTT). All of the thiol-modifiers and phosphoramidites used call be purchased from Glen Research (Sterlinig, Va.).

After synthesis, the 5'-sulfhydiryl, 5'-disulfide, 3'-sulfhydryl, or 3'-disulfide modified oligonucleotides can be purified (for example, using an HPLC column) to separate the full-length oligonucleotides from any contaminating prematurely terminated (i.e., shortened) oligonucleotides. Prior to use in the coupling reaction, the oligonucleotides are concentrated, and, if desired, the molar concentration of the oligonucleotides can be determined.

Although any of a variety of glass or plastic solid supports can be used in accordance with the methods of the present invention, glass is the preferred support. Preferrably, the glass support is a microscope slide, a glass plate, a quart wafer or a silicon wafer. An especially preferred support is a glass plate.

However, the support can be fashioned as a bead, dipstick, test tube, pin column, etc. Alternatively, the solid support can be a form of polystyrene plastic (e.g., 96-well microtiter plate, etc.).

Many different mercaptosilane compounds such as 3-mercaptopropyltrimethoxy-silane, 3-mercaptopropyltriethoxysilane, (mercaptomethyl)dimethoxysilane and (mercaptomethyl)methyldimehtoxysilane, etc. can be used in the present invention for coating the solid support with sulfliydryl groups. The general formula for a mercaptosilane that can be used in this invention is:

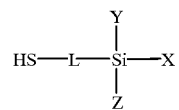

The X group involved in the reaction is usually a hydrolyzable group such as alkoxy, acyloxy, amine or chlorine, etc. The Y and Z groups can be the same hydrolizable group as the X group or they can be a non-hydrolyzable inert group such as an alkyl, alkene, alkane, cycloalkyl, aromatic group. The L is a linker arm, such as $(CH_2)_n$, $(CH_2)_n$-aromatic-$(CH_2)_n$, or an aromatic group, etc. As defined herein n is at least 1, preferably n is no greater than about 35. All of the mercaptosilanes mentioned above are commercially available from United Chemical, Inc. or Aldrich Chemical Company, Inc.

Alternatively, the mercaptosilane compounds identified above may be oxidized into the respective dislulfidesilane form. The general formula for a disulfidesulane that can be used in this invention is:

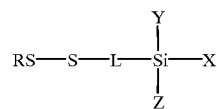

X, Y, and Z are the same as described above. The R group may be any non-hydrolyzable inert group, such as an alkyl, alkene, alkane, cycloalkyl, or aromatic group.

The mercaptosilane or dislufidesilane can be coated onto the solid-support by any of a number of means. For example, the mercaptosilane can be deposited onto the solid surface as an aerosol or a vapor. Alternatively, the mercaptosilane can be spread onto the solid-sturface by mechanical means (e.g., a spreader bar, a saturated cloth, etc.).

An important feature of the present invention is the hydrophobic nature of mercaptosilane and dislufidesilane. Because of this feature, it is possible for an aqueous solution to form extremely well defined beads on the surface of ally solid support coated with mercaptosilane or dislufidesilane. With an automated delivery system, such as a Hamilton robot or ink-jet printing method, it is possible to form a very complex array of oligonucleotide probes on a mercaptosilane or dislufidesilane coated glass slide. Such methods can deliver nano to pico-liter size droplets with sub-millimeter spacing. Because the aqueous beads are extremely well defined, it is possible to create an array with an extremely high density of oligonucleotidie probes. Thus, it is possible to create arrays having greater than about 10,000 probe droplets/cm$^2$. Such arravs can be assembled through the use of a robotic liquid dispenser (such as an ink-jet printing device controlled by a piezoelectric droplet generator) such that each nucleic acid molecule occupies a spot of more than about 10 microns, preferably more than 25 microns in diameter and each nucleic acid spot is spaced no closer, center to center, than the average spot diameter. Methods and apparatuses for dispensing small amount of fluids using such ink-jet printing techniques and piezoelectric ink-jet depositions have been previously described by Wallace, David B. et al. (U.S. Pat. No. 4,812,856), Hayes, Donald J. et al. (U.S. Pat. No. 5,053,100), and Hayes, Donald J. et al. (*BioTechniques*, June, 1994), all of which are herein incorporated by reference.

Another important feature of the present invention is that the mercaptosilane or dislufidesilane treated surface can be reused by treating the surface with a mild reducing agent. Such a treatment will release the covalently immobilized oligonucleotide from the surface and the surface can now be used to immobilize another array of oligonucleotides.

II. The Use of Immobilized Nucleic Acid Molecules

Immobilized nucleic acid molecules, and more preferably, immobilized oligoniucleotides, make an ideal diagnostic tool. Specifically, their versatility and simplicity make them ideal diagnostic tools for the detection of infectious and genetic diseases, mutation analysis, etc.

Although the manner in which the nucleic acid molecules are immobilized to the solid support can be random, one of the preferred embodiments of the invention is to arrange the nucleic acid molecules into an ordered array. As used herein, an array is an orderly arrangement of nucleic acid molecules, as in a matrix of rows and columns. The chemistry of the present invention is such that an individual array can contain either a finite or an infinite number of unique immobilized nucleic acid molecules. Preferably, the array will contain more than one distinct immobilzed nucleic acid molecule.

There are two preferred methods to make a nucleic acid array: one is to synthesize the specific oligonucleotide sequences directly onto the solid-phase in the desired pattern (Southern, et al., *Nucl. Acids Res.* 22:1368–1373 (1994); Maskos, et al., *Nucl. Acids Res.* 20:1679–1684 (1992); and Pease, et al., *Proc. Natl. Aced. Sci.* 91:5022–5026 (1994); all of which are herein incorporated by reference) and the other is to pre-synthesize the oligonucleotides on an automated DNA synthesizer (such as an ABI 392 and then attach the oligonucleotides onto the solid-phase at specific locations (Lamture, et al., *Nucl. Acids Res.* 22:2121–2125 (1994) and (Smith, et al., *Nucl. Acids Res.* 22:5456–5465 (1994) both herein are incorporated by reference). In the first method, the efficiency of the coupling step of each base will affect the quality and integrity of the nucleic acid molecule array. This method generally yields a large percentage of undesired incomplete (shortened) sequences which can create problems in the analysis step and effect the integrity of the analysis. Thus, the quality and integrity of an arrav synthesized according to the first method is inversely proportional to the length of the nucleic acid molecule. Specifically, the synthesis of longer oligonucleotides results in a higher percentage of incomplete, shortened sequences.

A second, more preferred, method for nucleic acid array synthesis utilizes an automated DNA synthesizer for DNA synthesis. The controlled chemistry of an automated DNA synthesizer allows for the synthesis of longer, higher quality DNA molecules than is possible with the first method. Also, the nucleic acid molecules synthesized according to the second method can be purified prior to the coupling step. Therefore, the quality of the nucleic acid molecule array can be expected to be much higher than the quality of the nucleic acid array of the first method. However, a simple, effective and specific oligonucleotide coupling chemistry is lacking for the attachment of presynthesized oligonucleotides. The present invention describes a simple, effective and efficient method for coupling a pre-synthesized oligonucleotide onto a solid-phase by means of a reversible disulfide bond.

A. Hybridization Detection Of PCR Products

Thus, for example, covalently immobilized nucleic acid molecules may be used to detect specific PCR products by hybridization where the capture probe is immobilized on the solid phase (Ranki et al., *Gene* 21: 77–85 (1983); Keller et al., *J. Clin. Microbiol.* 29: 638–641 (1991); Urdea et al., *Gene* 61: 253–264 (1987). A preferred method would be to prepare a single-stranded PCR product before hybridization. A sample, suspected to contain the target molecule, or an amplification product thereof, would then be exposed to the solid-surface and permitted to hybridize to the bound oligonucleotide.

The methods of the present invention do not require that the target nucleic acid contain only one of its natural two strands. Thus, the methods of the present invention may be practiced on either double-stranded DNA, or on single-stranded DNA obtained by, for example, alkali treatment of native DNA. The presence of the unused (non-template) strand does not affect the reaction.

Where desired, however, any of a variety of methods can be used to eliminate one of the two natural stands of the target DNA molecule from the reaction. Single-stranded DNA molecules may be produced using the single-stranded DNA bacteriophage M13 (Messing, J. et al., *Meth. Enzymol.* 101:20 (1983); see also, Sambrook, J., et al. (In: *Molecular Cloning: A Laboratory Manual*, Cold Spring Harbor Laboratory Press, Cold Spring Harbor, N.Y. (1989)).

Several alternative methods can be used to generate single-stranded DNA molecules. Gyllensten, U. et al., (*Proc. Natl. Acad. Sci. (U.S.A.)* 85:7652–7656 (1988) and Mihovilovic, M. et al., (*BioTechniques* 7:14 (1989)) describe a method, termed "asymmetric PCR," in which the standard "PCR" method is conducted using primers that are present in different molar concentrations. Higuchi, R. G. et al. (*Nucleic Acids Res.* 17:5865 (1985)) exemplifies an additional method for generating single-stranded amplification products. The method entails phosphorylating the 5'-terminus of one strand of a double-stranded amplification product, and then permitting a 5'→3' exonuclease (such as T7 gene exonuclease) to preferentially degrade the phosphorylated strand.

Other methods have also exploited the nuclease resistant properties of phosphorothioate derivatives in order to generate single-stranded DNA molecules (Benkovic et al., U.S. Pat. No. 4,521,509); Sayers, J. R. et al. (*Nucl. Acids Res.* 16:791–802 (1988); Eckstein, F. et al., *Biochemistry* 15:1685–1691 (1976); and Ott, J. et al., *Biochemistry* 26:8237–8241 (1987)).

Most preferably, such single-stranded molecules will be produced using the methods described by Nikiforov, T. (commonly assigned U.S. Pat. No. 5,518,900, herein incorporated by reference). In brief, these methods employ nuclease resistant nucleotide derivatives, and incorporate such derivatives, by chemical synthesis or enzymatic means, into primer molecules, or their extension products, in place of naturally occurring nucleotides.

Suitable nucleotide derivatives include derivatives in which one or two of the non-bridging oxygen molecules of the phosphate moiety of a nucleotide has been replaced with a sulfur-containing group (especially a phosphorothioate), an alkyl group (especially a methyl or ethyl alkyl group), a nitrogen-containing group (especially an amine), and/or a selenium-containing group, etc. Phosphorothioate deoxyribonucleotide or ribonucleotide derivatives are the most preferred nucleotide derivatives. Methods of producing and using such phosphorothioate derivatives are disclosed by Nikiforov, T. (U.S. Pat. No. 5,518,900).

B. Solid Phase DNA Sequencing

The methods of the present invention may also be used in the practice of solid-phase sequencing as described by Khrapko, K. R. et al. (*DNA Seq.* 1:375–388 (1991) and Drmanac, R. and Crkvenjakov, R., *Int. J. Genome Res.* 1: 1–11 (1992)), both herein are incorporated by reference.

C. GBA™ Genetic Bit Analysis

The methods of the present invention may also be used to immobilize the oligonucleotides that are used in the GBA™ Genetic Bit Analysis (Goelet, P. et al., PCT Application No. 92/15712, herein incorporated by reference). GBA™ Genetic Bit Analysis describes a solid-phase method for the typing of single-nucleotide polymorphisms. Oligonucleotides having a defined sequence complementary to a region that lies immediately proximal or distal to the variable nuicleotide of a polymorphism would thus be provided to a polystyrene microtiter well or glass plate, and incubated with a salt, in accordance with the above-described methods.

The immobilized primer is then incubated in the presence of a DNA molecule (preferably a genomic DNA molecule) having a single nucleotide polymorphism whose immediately 3'-distal sequence is complementary to that of the immobilized primer. Preferably, such incubation occurs in the complete absence of any dNTP (i.e. dATP, dCTP, dGTP, or dTTP), but only in the presence of one or more chain terminating nucleotide derivatives (sucl as a dideoxynucleotide derivatives), and under conditions sufficient to permit the incorporation of such a derivative ointo the 3-terminus of the primer. As will be appreciated, where the polymorphic site is such that only two or three alleles exist (such that only two or three species of ddNTPs, respectively, could be incorporated into the primer extension product), the presence of unusable nucleotide triphosphate(s) in the reaction is immaterial. In consequence of the incubation, and the use of only chain terminating nucleotide derivatives, a single dideoxynucleotide is added to the 3-terminus of the primer. The identity of that added nulcleotide is determined by, and is complementary to, the nucleotide of the polymorphic site of the polymorphism.

Using the method described in the present patent application, oligonucleotide primers can be immobilized on solid phases like polystyrene or glass, hybridized to PCR-derived, single-stranded templates, and subjected to enzymatic extension at their 3-ends by a single, labeled ddNTP. The nature of the incorporated ddNTP is determined by the nucleotide that is located in the opposite strand (the polymorphic nucleotide). This assay can be conveniently carried out both in polystyrene ELISA plates, or on glass slides.

In this embodiment, the nucleotide of the polymorphic site is thus determined by assaying which of the set of labeled nucleotides has been incorporated onlto the 3'-terminus of the bound oligonucleotide by a primer-dependent polymerase. Most preferably, where multiple dideoxynucleotide derivatives are simultaneously employed, different labels will be used to permit the differential determination of the identity of the incorporated dideoxynucleotide derivative.

D. Ligase-Mediated GBA™

The methods and reagents of the present invention can also be used in concert with a polymerase/ligase mediated polymorphic interrogation assay. This assay, termed ligase-mediated GBA™ grenetic bit analysis, is a more specific version of the GBA™ genetic bit analysis assay. The additional specificity arises from the addition of a second hybridization step and a ligation step.

In this assay, two oligonucleotides are employed. The first oligonucleotide is a primer that is complementary to the immediately 3'-distal invariant sequence of the polymorphism. The 3'-end of the oligonucleotide is attached to the plate. A second linker oligonucleotide is complementary to the 5'-proximal sequence of the polymorphism being analyzed, but is incapable of hybridizing to the first oligonucleotide. The second linker oligonucleotide is phosphorylated at both its 3' and 5' ends.

These oligonucleotides are incubated in the presence of DNA containing the single nucleotide polymorphism that is to be analyzed, and at least one 2'-deoxynucleotide 5'-triphosphate. The incubation reaction further includes a DNA polymerase and a DNA ligase. The tethered and soluble oligonucleotides are thus capable of hybridizng to the same strand of the target molecule under analysis. The sequence considerations cause the two oligonucleotldes to hybridize to the proximal and distal sequences of the single nucleotide polymorphism (SNP) that flank the variable nucleotide of the polymorphism, and to be separated by a single nucleotide at the precise position of the variability.

The presence of a polymerase and the 2'-deoxynucleotide 5'-triphosphate complementary to the nucleotide present in the variable site of the polymorphism permits the extended primer to be ligated to the bound oligonucleotide, thereby immobilizing the primer. The identity of the polymorphic site that was opposite the single nucleotide can then be determined by any of several means. In a preferred embodiment, the 2'-deoxynucleotide 5'-triphosphate of the reaction is labeled, and its detection thus reveals the identity of the complementary nucleotide of the polymorphic site. Several different 2'-deoxynucleotide 5'-triphosphates may be present, each differentially labeled. Alternatively, separate reactions can be conducted, each with a different 2'-deoxynucleotide 5'-triphosphate. In an alternative sub-embodiment, the 2'-deoxynucleotide 5'-triphosphates are unlabeled, and the soluble oligonucleotide is labeled. In this embodiment, the primer that is extended is immobilized on the polystyrene. Separate reactions are conducted, each using a different unlabeled 2'-deoxynucleotide 5'-triplhosphate.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

EXAMPLE 1

COUPLING BY MEANS OF A DISULFIDE EXCHANCE REACTION

The general chemistry of the thliol-disulfide exchange reaction has been previously described by Ryden, L. et al., herein incorporated by reference. (In: Jansosn, J. et al., eds. *Protein Purification: Principles, High Resolution Methods, and Application*, VHC Publislhers, lnc., New York, N.Y. (1989)).

Attachment of the 5'- or 3'-disulfide modiified oligonucleotide is obtained by a two step process of silanie treatment and oligonucleotide binding. Initially, the glass slides are etched overnight in 25% aqueous ammonium hydroxide and then rinsed sequentially with milliQ water and 95% ethanol. The glass slides are then treated for 30 minutes with 3-mercapto-proyl-trimethoxysilane (MPTS) in an acidic buffer of aqueous ethanol (95% ethanol, pH 4.5). The slides are then cured for at least 48 hours under a dry inelrt gas, such as $Ar_2$ or $N_2$.

The cured slides are treated with 5'-disillfide modified oligonucleotides in a carbonate buffer (500 mM, pH 9.0) for 2 hours at room temperature. The disulfide reaction between the RS group on the oligonucleotide and the available thiol of the mercaptosilane yields a disulfide bond between the oligonucleotide and the silane layer.

Experimental results indicate that the attachment efficiency of this attachment chemistry is very high. This method is very specific (at least 80 to 90% specificity) and provides a very high density of oligonucleotide attachment ($10^5$ molecules/$\mu m^2$).

EXAMPLE 2

COUPLING BY MEANS OF A DISULFIDE FORMATION REACTION

In a second embodiment, the coupling reaction is accomplished by means of a disulfide formation reaction. This method is used to attach oligonucleotides to a glass slide by coupling 5'-sulfhydyl modified oligonucleotides to sulfhydryl groups of the mercaptosilane coated surface.

The glass slides are initially coated with mercaptosilane to introduce sulflhydyl groups onto the surface following the protocol detailed above. 5'-sulfhydryl modified oligonucleotides are obtained by treating the disulfide modified oligonucleotide with dithiolthreitol (0.04M in 0.17M phosphate buffer, pH 8.0) at room temperature overnight. Then, the 5'-sulfhydryl modified oligonuitcleotides (at a concentration greater than 2 $\mu$m) are exposed to the mercaptosilane surface in a carbonate buffer (500 mM, pH 9.0) for 2 hours at room temperature. The formation of disulfide bonds between the surface mercaptosilane and the 5'-sulflhydryl groups result in the covalent attachment of the oligonucleotides.

EXAMPLE 3

QUANTITATION OF DISULFIDE COUPLING REACTION

Radioactive labeling and phosphorimaging, are used to quantify the oligonucleotide coupling reactions. [$\alpha$-$^{32}$] ddATP is used in a transferasebased 3' labeling reaction of the primer and template to quantitate the attachment and hybridization and is used as a label to quantitate the GBA extension. The attachment is dependent on the concentration of the disulfide oligonucleotide, with a maximal attachment density of about 3.5 picomole/7 $mm^2$ (an equivalent of $3.0\times10^5$ molecules per $\mu m^2$). The present methods provide a consistent hybridization efficiency of about 16% (percentage of hybridized primer) for various attachment densities. Under GBA reaction conditions, about 30% of the hybridized primer is extended for a total extension efficiency of 5%.

EXAMPLE 4

THE RELATIONSHIP BETWEEN PRIMER DENSITY AND HYBRIDIZATION EFFICIENCY

Hybridization efficiency is positively related to the surface density of the attached primer. In this study, increasing amounts of the BRACl primer is covalently attached to a solid surface according to the methods described above. As shown in Table 1, increased primer density is associated with increased hybridization efficiency. Accordingly, hybridization efficiency is affected by the stability of the primer attachment.

TABLE 1

| Hybridization v. Attachment | | | | | | |
|---|---|---|---|---|---|---|
| Hybridized Nucleic Acid (pmoles) | 0.12 | 0.15 | 0.19 | 0.20 | 0.21 | 0.19 |
| Attached Nucleic Acid (pmoles) | 0.51 | 0.73 | 1.26 | 1.56 | 1.61 | 1.57 |

EXAMPLE 5

GENETIC BIT ANALYSIS COMPATIBILITY

A GBA primer having a poly-T 10 residue long spacer arm is attached to the glass surface by means of the previously described disulfide exchange reaction. Standard GBA biochemistry is used to analyze two synthetic templates. Each synthetic template is hybridized to GBA primer immobilized to the treated glass slide creating four spots. Each spot is treated with an extension mix containing all of the extension reaction components, exonuclease-free Klenow fragment of the E. coli polymerase and each of four fluorescein-labeled ddNTP's and co-ddNTP's. The enzyme-mediated fluorescence signal is captured using a Cytoflour II fluorescent plate reader.

DNA Samples. Genomic DNA was isolated using the SDS/Proteinase K procedure (Maniatis, T. Molecular Cloninig, A laboratory Manual, Cold Spring Harbor Laboratory Press, Cold Spring Harbor (1989)) from peripheral blood nucleated cells of humans or horses enriched from red blood cells by selective lysis accomplished by diluting blood with a three fold volume excess of ACK lysing buffer (0.15 M ammonium chloride, 1 mM potassium bicarbonate, 0.1 mM EDTA). Oligonucleotides were prepared by solid-phase phosphoramidite chemistry using an Applied Biosystems, Inc. (Foster City, Calif.) Model 391 automated DNA synthesizer. In the case of primers used in Genetic Bit Analysis (GBA) reactions, detritylation was not performed following the final cycle of synthesis and the full-lengtlh oligonucleotide was purified using the Applied Biosystems oligonucleotide purification cartridge (OPC) as recommended by the manufacturer. For most PCR reactions, primers were used directly by drying down the de-protection reaction. Oligonucleotides derivatized with 5'-amino groups were prepared using Aminolink 2 purchased from Applied Biosystems and used according to the maniufacturer's recommendations.

Template Preparation. Amplification of geniomic sequences was performed using the polymerase chain reaction (PCR) (Saiki, R. K., Gelfand, D. H., Stoffel, S., Scharf, S. J., Higuchi, R., Horn, G. T., Mullis, K. B., Erlich, H. A., Primer Directed Enzymatic Amplification of DNA with a Thermostable DNA Polymerase. Science 239:487–491). In a first step, one hundred nanograms of genomic DNA was used in a reaction mixture containing each first round primer at a concentration of 2 μM/10 mM Tris pH 8.3/50 mM KCl/1.5 mM MgCl$_2$/0.1% gelatin/0.05 units per μl Taq DNA Polymerase (AmpliTaq, Perkin Elmer Cetus, Norwalk, Conn.). Reactions were assembled and incubated at 94° C. for 1.5 minutes, followed by 30 cycles of 94° C./1 minute, 60° C./2 minutes, 72° C./3 minutes. Single stranded DNA was prepared in a second "asymmetric" PCR in which the products of the first reaction were diluted 1/1000. One of the primers was used at the standard concentration of 2 μM while the other was used at 0.08 μM. Under these conditions, both single stranded and double stranded molecules were synthesized during the reaction.

Solid phase immobilization of nucleic acids. GBA reactions were performed in 96-well plates (Nunc Nunclon plates, Roskilde, Denmark). The GBA primer was covalently coupled to the plate using the disulfide formation reaction, previously described. After coupling, the plate was washed three times with 10 mM Tris pH 7.5/150 mM NaCl/0.05% polysorbitan-20 (Tween-20) ("TNTw").

Biotinylated ddNTPs. Biotinylated ddNTPs were synthesized according to U.S. Pat. No. 5,047,519.

GBA in Microwell Plates. Hybridization of single-stranlded DNA to primers covalenitly coupled to 96-well plates was accomplished by adding an equal volume of 3M NaCl/50 mM EDTA to the second round asymmetric PCR and incubating each well with 20 μl of this mixture at 55° C. for 30 minutes. The plate was subsequently washed three times witlh TNTw. Twenty (20) μl of polymerase extension mix containing ddNTPs (3 μM each, one of which was biotinylated/5 mM DTT/7.5 mM sodium isocitrate/5 mM MnCl$_2$/0.04 units per μl of modified T7 DNA polymerase and incubated for 5 minutes at room temperature. Following the extension reaction, the plate was washed once with TNTw. Template strands were removed by incubating wells with 50 μl 0.2N NaOH for 5 minutes at room temperature, then washing the wells with another 50 μl 0.2N NaOH. The plate was then washed three times with TNTw. Incorporation of biotinylated ddNTPs was measured by an enzyme-linked assay. Each well was incubated with 20 μl of streptavidin-conjugated horseradish peroxidase (1/1000 dilution in TNTw of product purchased from BRL, Gaithersburg, Md.) with agitation for 30 minutes at room temperature. After washing 5 times with TNTw, 100 μl of o-phenylenediamine (OPD, 1 mg/ml in 0.1 M Citric acid, pH 4.5) (BRL) containing 0.012% H$_2$O$_2$ was added to each well. The amount of bound enzyme was determined by photographing the plate after stopping the reaction or quantitatively using a Molecular Devices model "Vmax" 96-well spectrophotometer.

Table 2 depicts the results of an experiment employing a synthetic template 1 (designed to give a GBA signal in base A) and a synthetic template 2 (designed to give a signal in base T). Both signals give strong signals in the expected bases with virtually no noise observed in the other bases (the Signal to Noise Ratio ranged from 150:1 to 22:1).

TABLE 2

| | Fluorescent Counts | |
|---|---|---|
| Nucleotide Inserted | Template 1 | Template 2 |
| A | ≈6000 | 88.8 |
| C | 42.5 | 56 |
| G | 44 | 41 |
| T | 40 | ≈1900 |

EXAMPLE 6

DIRECT DETECTION OF GBA SIGNAL USING THE DISULFIDE ATTACHMENT METHOD

A standard Fluormager, such as a Molecular Dynamics FluorImager 595, can be used for the direct detection of a CBA signal. A 25-mer GBA primer (4257) with a poly-T 10 nucleotide residue long spacer arm is attached to the glass surface by means of the previously described disulfide exchange reaction. Standard GBA biochemistry is used to analyze two synthetic templates, 2982 (A) and 2983 (T). Each synthetic template is hybridized on two different slides with slides 1 and 2 containing template 2982(A) and slides 3 and 4 containing template 2983(T). After hybridization, slides 1 and 3 are treated with extension mix containing all of the extension reaction components, exonuclease free Klenow fragment of E. coli polymerase and fluorescein-labeled ddATP and unlabeled ddGTP, ddCTP and ddTTP. Slides 2 and 4 are treated with extension mix containing all of the extension reaction components, exonuclease free Klenow fragment of E. coli polymerase and fluorescein-labeled ddTTP's and unlabeled ddGTP, ddCTP and ddATP. The image is detected by the FluorImager using a 488 nm excitation wave and a 530 nm emission filter. As shown in FIG. 1, both templates give strong signals in the expected bases. Template 2982 gives a strong GBA signal in base A and synthetic template 2983 gives a strong signal in base T with virtually no background noise in the other bases (Signal to Noise Ratio ranged from about 100:1 to 25:1).

EXAMPLE 7

OLIGONUCLEOTIDE ARRAY PATTERNING WITH DISULFIDE ATTACHMENT METHODS

Twelve 5'-distilfide modified oligonucleotides (ten human loci GBA primers, one attachment control oligoiucleotide and one hybridization control oligonucleotide), are diluted in carbonate buffer (500 mM, pH 9.0) at a concentration of about 2 μm. The oligoiucleotides are dispensed onto the mercaptosilane coated surface at the desired positions using a 10 μl Hamilton syringe, in about 0.5 μl droplets to create individual spots, each spot is about 1 mm$^2$ or smaller and there is about 200 to 1000 μm spacing (edge to edge) between each spot. The oligonucleotide spots are coupled to the coated surface for about 2 hours at room temperature and the unbound oligonucleotides are washed away by means of 10 mM Tris pH 7.5/150 mM NaCl/0.05%) polysorbitan 20 (Tween-20) (herein referred to as "TNTw").

After attachment, the arrays are inter-rogated by standard GBA reactions using a mixture of multiplex PCR (10×) templates consisting of 10 human loci amplified from human placental DNA. After the GBA reaction, the signals are detected by indirect fluorescent detection using an antifluorescent antibody-enzyme conjugate and an ELF substrate. Table 3 lists the ten loci tested, the expected genotype for each locus and the GBA signals obtained.

TABLE 3

| Locus | Expected Genotype | GBA Signal Obtained |
|---|---|---|
| H20 | CC | CC |
| H21 | GG | CG |
| H27 | AA | FAILED |
| H60 | TC | TC |
| H12 | TG | TG |
| H45 | CC | CC |
| H84 | TC | TC (WEAK) |
| H94 | TC | TC (WEAK) |

TABLE 3-continued

| Locus | Expected Genotype | GBA Signal Obtained |
|---|---|---|
| H210 | CC | CC |
| H212 | GG | GG |
| Att. Control | N/A | N/A |
| Hyb. Control | N/A | N/A |

EXAMPLE 8

PREPARATION OF AN OLIGONUCLEOTIDE ARRAY BY INK-JET PRINTING

Another method for the automated delivery of the oligonucleotide solution employs an ink-jet printing technique performed by MicroFab Technologies, Inc. (Plano, Tex.). In one experiment, four different spot spacing (center to center) and eight different droplet sizes are tested on the mercaptosilane coated surface using a 5'-disulfide oligonucleotide labeled at the 3'-terminus with fluorescein. The format of the slides, depicted in Table 4, are as follows:

TABLE 4

| Slide No. | Spot Spacing | Row (Row Spacing = 6 mm) | | |
|---|---|---|---|---|
| | | Row 1 | Row 2 | Row 3 |
| Slide 1 | 1 mm | 5 nl | 10 nl | 25 nl |
| Slide 2 | 0.5 mm | 1 nl | 2 nl | 5 nl |
| Slide 3 | 250 μm | 250 pl | 500 pl | 1 nl |
| Slide 4 | 125 μm | 125 pl | 250 pl | N/A |

The labeled oligonucleotides are detected using a Molecular Dynamic FluorImager 595. As shown in FIG. 2, the ink-jet printing technique is a suitable method for the manufacture of oligo arrays with sub-millimeter spacing and nano to pico-liter droplet sizes. As such, the ink-jet printing technique is suitable for large scale manufacture of oligo arrays.

EXAMPLE 9

PREPARATION OF AN OLIGONUCLEOTIDE ARRAY WITH AN AUTOMATIC PIPETING ROBOT

Hamilton 2200 automated pipeting robot is used to make arrays of oligonulcleotide drops, ranging in size from about 100 nl to about 250 nl, with 1 mm spacing between dots. As in the ink-jet printing method, a Hamilton robot can be programmed to deliver nanoliter size droplets with sub-millimeter spacing.

EXAMPLE 10

PREPARATION OF SINGLE-STRANDED PCR PRODUCTS

In order to protect one of the strands of the double-stranded PCR product from exonuclease hydrolysis, four phosphorothioate bonds are introduced during synthesis at the 5'-end of one of each pair of the PCR primers. For generation of single-straniced PCR products, following the PCR amplification, T7 gene 6 exonuclease is added to a final concentration of 2 units/μl of PCR reaction. Incubation is for one hour at room temperature. The T7 gene 6 exonuclease can be purchased from USB and diluted in a buffer recommended by the manufacturer. Following the exonuclease treatment, aliquots of the reaction mixtures are withdrawn and analyzed by polyacrylamide gel electrophoresis.

EXAMPLE 11

HYBRIDIZATION OF SINGLE-STRANDED PCR FRAGMENTS TO OLIGONUCLEOTIDES IMMOBILIZED IN ELISA PLATES

After the exonuclease treatment, an equal volume of 3 M NaCl, 20 mM EDTA is added to the reaction mixture and 20 μl aliquots of the resulting solution transferred to individual wells containing the appropriate immobilized oligonucleotide molecule. The sequences of the immobilized capture probes are given above. These capture probes are immobilized using 500 mM NaCl. Hybridization is carried out for 30 minutes at room temperature and is followed by washing with 10 mM Tris pH 7.5/150 mM NaCl/0.05% polysorbitan 20 (Tween-20) (herein referred to as "TNTw").

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for attaching a modified nucleic acid molecule to a coated solid-phase via a disulfide bond, said modified nucleic acid molecule being modified such that a 3' carbon atom or a 5' carbon atom of a sugar moiety of a nucleotide of said nucleic acid molecule possesses a sulfhydryl group or a disulfide group, said method comprising coupling said modified nucleic acid molecule to said coated solid-phase, wherein where said modified nucleic acid molecule is a modified nucleic acid molecule having a sulfhydryl group, said coated solid-phase is coated with a disulfidesilane, and where said modified nucleic acid molecule is a modified nucleic acid molecule having a disulfide group said coated solid-phase is coated with a mercaptosilane and wherein said disulfide bond is formed between a sulfur atom of either said sulfhydryl group or said disulfide group and a sulfur atom of either said disulfidesilane or said mercaptosilane.

2. A method for attaching a nucleic acid molecule to a solid-phase via a disulfide bond, said nucleic acid molecule being modified such that a 3' carbon atom or a 5' carbon atom of a sugar moiety of a nucleotide of said nucleic acid molecule possesses a sulthydryl group or a disulfide group, said method comprising the steps of:

(A) coating the surface of the solid-phase with a mercaptosilane or a disulfidesilane, wherein said mercaptosilane comprises a sulfliydryl group and said disulfidesilane comprise a disulfide group; and (B) (i) coupling a sulfhydryl modified nucleic acid molecule to the disulfide group of said disulfidesilane by means of a covalent disulfide bond; or (ii) coupling a disulfide modified nucleic acid molecule to the sulfhydryl groups of said mercaptosilane by means of a covalent disulfide bond;

wherein said disulfide bond is formed between a sulfur atom of either said sulfhydryl group or said disulfide group and a sulfur atom of either said disulfidesilane or said mercaptosilane.

3. The method according to claim 1 wherein said nucleic acid molecule is modified at a 5' carbon of a sugar moiety of the nucleic acid molecule.

4. The method according to claim 1 wherein said nucleic acid molecule is modified at a 3' carbon of a sugar moiety of the nucleic acid molecule.

5. The method according to claim 1 wherein said nucleic acid molecule is an oligonucleotide.

6. The method according to claim 1 wherein the coupling step is by means of a disulfide exchange reaction between said disulfide modified nucleic acid molecule and the sulfhydryl group of said mercaptosilane coated surface.

7. The method according to claim 1 wherein the coupling step is by means of a disulfide exchange reaction between said sulfhydryl modified nucleic acid molecule and the disulfide group of said mercaptosilane coated surface.

8. The method according to claim 1 wherein the disulfide group of said disulfide modified nucleic acid molecule is reduced by means of a reducing agent.

9. The method according to claim 8 wherein the coupling step is by means of a disulfide formation reaction between the sulfhydryl group of said mercaptosilane coated solid-phase and the reduced disulfide modified nucleic acid molecule.

10. The method according to claim 8 wherein said reducing agent is selected from the group consisting of mercaptoethanol and dithiothreitol.

11. The method according to claim 1 wherein said coupling reaction forms a disulfide bond wherein said disulfide bond is reversible.

12. The method according to claim 1 wherein said solid-phase is glass.

13. The method according to claim 1 wherein said solid-phase is plastic.

14. The method according to claim 13 wherein said plastic is polystyrene plastic.

15. The method according to claim 1 wherein said solid-phase is selected from the group consisting of a bead, a plate, a column, a pin and a dipstick.

16. The method according to claim 1 wherein the coupling reaction creates an array of more than one distinct immobilized nucleic acid molecule.

17. The method of claim 2 wherein said immobilized nucleic acid is a polynucleotide and wherein said method additionally comprises the steps:

(C) capturing from a solution at least one strand of a specific polynucleotide analyte by hybridization to said immobilized polynucleotide; and (D) detecting the presence of the captured analyte.

18. The method of claim 2 wherein said immobilized nucleic acid is a polynucleotide and wherein said method additionally comprises the steps of:

(C') (i) amplifying a specific region of a specific genome using a polymerase chain reaction, said region having a sequence complementary to said immobilized polynutcleotide;

(ii) capturing from solution at least one strand of said amplification product by hybridization to said immobilized polynucleotide; and (D') detecting the presence of the captured amplification product.

19. The method of claim 2 wherein said immobilized nucleic acid is a polynucleotide and wherein said method additionally comprises the steps:

(C'') (i) in the presence of said immobilized polynucleotide primer and at least one dideoxynucleotide derivative, incubating a nucleic acid molecule of a target organism, wherein said nucleic acid molecule contains a single nucleotide polymorphism, under conditions sufficient to permit a polymerase mediated, template-dependent extension of said primer, said extension causing the incorporation of a single dideoxynucleotide into the 3'-terminus of said primer, said single dideoxynucleotide being complementary to the single nucleotide of the polymorphic site of said polymorphism;

(ii) permitting, said template-dependent extension of said primer molecule, and said incorporation of said single dideoxynucleotide; and (D'') determining the identity of the nucleotide incorporated into said polymorphic site, said identified nucleotide being complementary to said nucleotide of said polymorphic site.

20. The method of claim 14 wherein said polystyrene support is a 96-well microtiter plate containing hydrophilic groups.

21. The method of claim 14 wherein said polystyrene support is a 96-pin array designed to fit into a 96-well microtiter plate.

22. The method of claim 12 wherein said glass is selected from a group consisting of a microscope slide, glasss plate, quart wafer or silicon wafer.

23. The method according to claim 2 wherein said coating step is by means of an aerosol, a vaporization means or any other mechanical means.

24. The method according to claim 1 wherein the mercaptosilane comprises at least one hydrolizable group and a sulfydryl group wherein said sulfhydyl group is attached to the mercaptosilane via a linker arm.

25. The method according to claim 16 wherein the array is assembled by means of a robotic liquid dispenser on a piezoelectric ink jet deposition.

26. The method according to claim 25 wherein each nucleic acid molecule occupies a spot of at least 10 microns in diameter and each nucleic acid spot is spaced no closer, center to center, than the average spot diameter.

27. The method according to claim 1 wherein said mercaptosilane has the structure

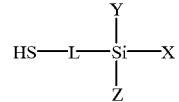

wherein X is alkoxy, acyloxy or halogen group; Y and Z are alkoxy, acyloxy, halogen group or a non-hydrolizable inert group; and L is a linker arm.

28. The method according to claim 1 wherein said disulfidesilane has the structure

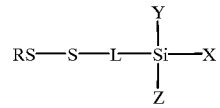

wherein X is alkoxy, acyloxy or halogen group; Y and Z are alkoxy, acyloxy, halogen group or a non-hydrolizable inert group; R is a non-hydrolizable group; and L is a linker arm.

29. The method accoding to claim 27 or 28 wherein said linker arm is $(CH_2)_n$, $(CH_2)_n$-aromatic-$(CH_2)_n$ or an aromatic group, and wherein n is at least 1.

30. The method according to claim 28, wherein said non-hydrolyzable group is selected from the group consisting of an alkyl, alkene, alkane, cycloalkyl, and aromatic group.

31. A modified nucleic acid molecule coupled via a disulfide bond to a coated solid-phase, said modified nucleic acid molecule being modified such that a 3' carbon atom or a 5' carbon atom of a sugar moiety of a nucleotide of said nucleic acid molecule possesses a sulfhydryl group or a disulfide group, wherein where said modified nucleic acid molecule is a modified nucleic acid molecule having a sulfhydryl group, said coated solid-phase is coated with a disulfidesilane, and where said modified nucleic acid molecule is a modified nucleic acid molecule having a disulfide group said coated solid-phase is coated with a mercaptosilane, and wherein said disulfide bond is formed between a sulfur atom of either said sulfhydryl group or said disulfide group and a sulfur atom of either said disulfidesilane or said mercaptosilane.

* * * * *